United States Patent [19]

Di Battista

[11] 4,400,513

[45] Aug. 23, 1983

[54] 1-OXA-6-AZASPIRO[2.5]OCTANES

[75] Inventor: Piero Di Battista, Milan, Italy

[73] Assignee: Montedison, S.p.A., Milan, Italy

[21] Appl. No.: 358,488

[22] Filed: Mar. 15, 1982

[30] Foreign Application Priority Data

Mar. 16, 1981 [IT] Italy ............................... 20353 A/81

[51] Int. Cl.³ .......................................... C07D 491/07
[52] U.S. Cl. .......................................... 546/16; 546/5
[58] Field of Search ..................................... 546/5, 16

[56] References Cited

U.S. PATENT DOCUMENTS 3,692,778  9/1972  Murayama et al. ................... 546/16

OTHER PUBLICATIONS

Fishman et al., "J. Het. Chem.", vol. 5, pp. 467–469 (1968).

Primary Examiner—Robert T. Bond

[57] ABSTRACT

There are disclosed new 4-spiro-oxirane derivatives of substituted piperidine having the general formula:

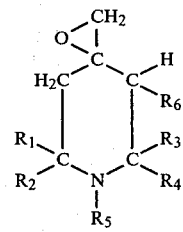

wherein $R_1$, $R_2$, $R_3$, $R_4$, either like or unlike one another, are each an alkyl radical having 1 to 4 C, or $R_1$ and $R_2$, and/or $R_3$ and $R_4$ together form a cyclo-alkylene radical having 3 to 13 C; $R_5$ may be hydrogen, an alkyl, oxyalkyl or alkoxy radical having 1 to 6 C, an aryl or aryl-alkyl radical having 6 to 18 C, an alkenyl radical having 2 to 6 or a $-(CH_2)_xCO_2R_7$ radical in which X is an integer from 0 to 12, $R_7=H$, metal, an alkyl, alkylene, alkenyl, alkenylene radical having 1 to 20 C and $R_6$ is hydrogen or an alkyl radical containing 1 to 4 C.

7 Claims, No Drawings

1-OXA-6-AZASPIRO[2.5]OCTANES

The present invention relates to new derivatives of piperidine. In particular, it relates to new 4-spiro-oxirane derivatives of substituted piperidine having general formula:

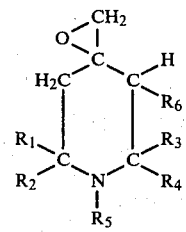

in which $R_1$, $R_2$, $R_3$ and $R_4$, either like or unlike one another, are each an alkyl radical containing 1 to 4 carbon atoms, or $R_1$ and $R_2$, and/or $R_3$ and $R_4$, together, form a cyclo-alkylene radical containing 3 to 12 carbon atoms; $R_5$ may be hydrogen, an alkyl, oxyalkyl or alkoxy radical containing 1 to 6 carbon atoms, an aryl or aryl-alkyl radical containing 6 to 18 carbon atoms; an alkenyl radical containing 2 to 6 carbon atoms or a —(CH$_2$)$_x$—CO$_2$R$_7$ radical in which X is zero or an integer ranging from 1 to 12, $R_7$ is hydrogen, a metal selected from the alkaline metals, such as Na and K, from the alkaline-earth metals, such as Ca and Ba, and from the transition metals such as Ni and Co, an alkyl, alkylene, alkenyl, alkenylene radical, each having from 1 to 20 carbon atoms, and $R_6$ is hydrogen or an alkyl radical containing from 1 to 4 carbon atoms.

The new compounds obtained have various industrial application possibilities. They are, in themselves, stabilizers and are employable as basic materials for preparing stabilizers to sunlight, to heat, and to oxidation of polymeric substances.

The compounds according to this invention are prepared, according to known methods, starting from a solution of dimethylsulphonium methylide in acetonitrile, to which the carbonyl compound corresponding to the derivative to be obtained is added. The reaction is conducted in the presence of an alkoxide or of a hydride of an alkaline metal.

The process according to the invention may be represented by the following reaction scheme:

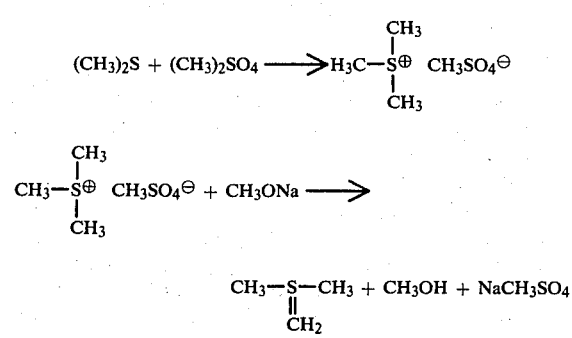

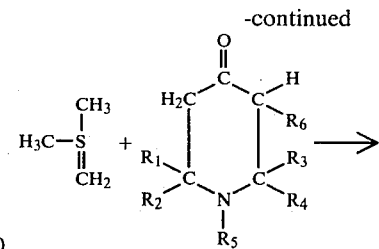

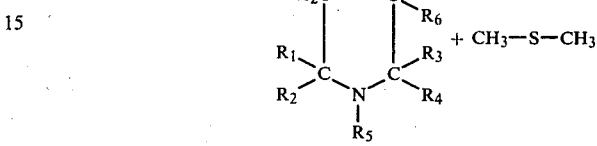

in which $R_1$, $R_2$, $R_3$, $R_4$, $R_5$ and $R_6$ have the meanings specified hereinabove.

By operating according to this method, various compounds have been obtained. Particularly interesting are the alkyl-substituted piperidines having general formula (I), in which $R_1$, $R_2$, $R_3$ and $R_4$ are each a methyl; $R_5$ is hydrogen or methyl; $R_6$ is hydrogen and particularly:

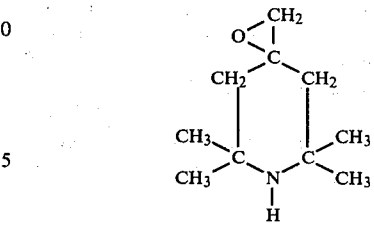

2,2,6,6-tetramethylpiperidine-4-spiro-oxirane, and

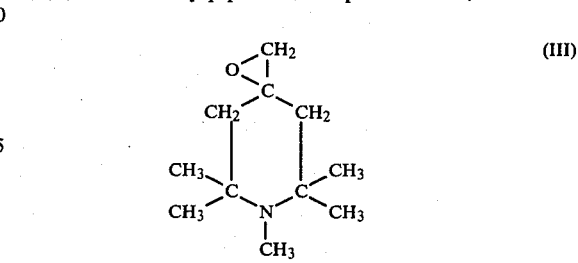

1,2,2,6,6-pentamethylpiperidine-4-spiro-oxirane.

So far as I am aware, such derivatives have never been described in the literature, and are new products. They are characterized—by the I.R. and N.M.R. analyses.

The substituted piperidines, having general formula (I), may be utilized as basic products for preparing stabilizers of organic materials usually subject to degradation of their chemical-physical properties due to the effect of sunlight, of heat and/or of oxygen, in particular, synthetic organic polymeric substances including:
polyolefins;
polyvinyl chloride and polyvinylidene chloride;
polyacetals such as polyoxymethylene and polyoxyethylene;
polyesters such as polyethyleneterephthalates;
polyamides such as nylon 6, nylon 6-6 and nylon 6-10;
polyurethanes;

polycarbonates;
thermoplastic elastomers;
natural and synthetic rubbers, etc.

The following examples, illustrating the invention in more detail, are not intended to be limiting.

In the examples, unless otherwise specified, all parts are to be understood as parts by weight.

EXAMPLE 1

A. Preparation of 2,2,6,6-tetramethylpiperidine-4-spiro-oxirane

Into a 2-liter flask there were introduced 94.6 g (0.75 mole) of dimethyl sulphate $(CH_3)_2SO_4$, dissolved in 350 cc of acetonitrile and 51.25 g (0.825 mole) of dimethyl-sulphide, dissolved in 150 cc of $CH_3CN$. The mass was stirred for a few hours and allowed to stand overnight.

44.55 g (0.825 mole) of $CH_3ONa$ were then added, under stirring, to the mixture and then, in half an hour, a solution of 77.5 g (0.5 mole) of triacetonamine dissolved in 50 cc of $CH_3CN$ was gradually added. After having stirred the mixture for 4 hours at room temperature, most of the solvent was distilled under vacuum and 500 cc of $H_2O$ were added to the mixture.

The reaction mixture was then extracted three times with 200 cc of $CHCl_3$ each, and the organic phase was evaporated from the solvent and rectified under vacuum.

75.6 g of product having a boiling point of 44°–45° C./1 mm Hg were obtained. The product, analyzed under a gas chromatograph on a column SUPELCO SP 1000, revealed a titer higher than 95%.

On the basis of the I.R. and N.M.R. spectra and of the centesimal analyses, the compound was recognized as 2,2,6,6-tetramethylpiperidine-4-spiro-oxirane, having the following formula:

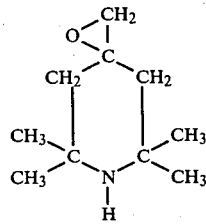

B. Preparation of poly-oxy-methylene-2,2,6,6-tetramethylpiperidine

Into a 100 ml flask there were added, under a nitrogen flow, 10 g of 2,2,6,6-tetra-methyl-piperidine-4-spiro-oxirane, as obtained under A, and 0.66 g of KOH. The mixture was heated in a nitrogen atmosphere, at 150° C. for 6 hours, under stirring. It was allowed to cool down to room temperature and the resulting solid was dissolved in $CHCl_3$. The solution was repeatedly washed with water and dried with $Na_2SO_4$. The solvent was first removed in a rotating evaporator and successively by means of heating to 120° C./0.1 mm Hg. A very viscous, light-yellow liquid was obtained, which had a glass transition temperature (Tg) of 20° C. and an average molecular weight, determined according to the osmometric method, of 650.

On the basis of the N.M.R. and R.R. spectra and of the centesimal analyses, the product was attributed the following structural formula:

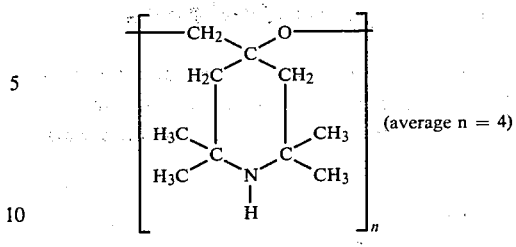

(average n = 4)

C. Stabilization Tests

To 300 g of unstabilized polypropylene, having an intrinsic viscosity, determined at 130° C. in tetralin, of 162 cc/g, a residue of the extraction with heptane equal to 96.5% and an ash content of 80 ppm, there were added 200 cc of chloroform containing, dissolved therein, the above-obtained poly-oxy-methylene-2,2,6,6-tetramethylpiperidine, in the amount indicated in Table I.

The mixture was stirred for about 6 hours, at room temperature, in a rotating evaporator, then dried at 50° C. and at 0.01 mm Hg in 1 hour. The resulting additioned powder was extruded in a Brabender extruder at 220° C. and granulated. The granules were transformed into films having a uniform thickness of 50–60 microns, and into 1 mm thick plates.

On the articles so obtained, the thermo-oxidative stability, as well as the photo-oxidative stability, were determined.

The thermo-oxidative stability was determined on the basis of the resistance to ageing in an oven, considered as the embrittlement time (E.T.) required to notice, with the naked eye, on the examined plate, crackings or chalkings of the surface and other modifications due to exposure to an air stream in an oven at 150° C.

The photo-oxidative stability was determined on the basis of the embrittlement time, considered as the time required to cause the rupture of the film by means of a single bending by 180°, after exposure to Xenotest 1200 under the conditions according to DIN 54004:
temperature of the black panel: 43°±2° C.;
relative humidity: 50±5%;
alternate exposure.

TABLE I

| Added Amount (%) | Thermo-oxidative Stability Embrittlement Time (h) | Photo-oxidative Stability Embrittlement Time (h) |
| --- | --- | --- |
| — | >24 | 100 |
| 0.3 | 350 | 2000 |
| 0.5 | 650 | 2500 |

EXAMPLE 2

A. Preparation of 1,2,2,6,6-pentamethyl-piperidine-4-spiro-oxirane

Operating according to the modalities described in Example 1A, there were employed, respectively: 40 g (0.237 mole) of N-methyltriacetonamine, 24.24 g (0.39 mole) of dimethylsulphide, 44.78 g (0.355 mole) of dimethylsulphate and 21.06 (0.39 mole) of sodium methoxide.

From the organic phase, after rectification, 35.3 g of a product having a boiling point of 54° C./1 mm Hg and a titer higher than 98% were obtained.

On the basis of the N.M.R. and I.R. spectra and of the centesimal analyses, the following structural formula was attributed to the product:

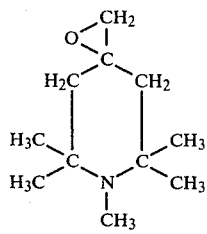

B. Preparation of poly-oxy-methylene-1,2,2,6,6-penta-methylpiperidine

Operating according to the modalities of Example 1B, 10 g of 1,2,2,6,6-penta-methyl-piperidine-4-spiro-oxirane were treated with 0.6 g of KOH.

A solid, light-yellow product was obtained, which softened at 77° C. and exhibited an average molecular weight of 1230, determined according to the osmometric method.

On the basis of the I.R. and N.M.R. spectra and of the centesimal analyses, the following structural formula was attributed to the product:

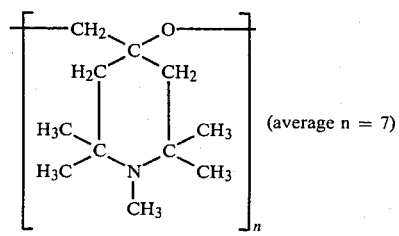

(average n = 7)

C. Stabilization Tests

By operating according to the modalities described in Example 1C, films and plates were prepared from polypropylene stabilized with the poly-oxy-methylene-1,2,2,6,6-penta-methylpiperidine obtained under 2B, in amounts recorded in Table II. The thermo-oxidative and the photo-oxidative stabilities were determined on the prepared articles, the values obtained being recorded in Table II.

TABLE II

| Added Amount (%) | Thermo-oxidative Stability Embrittlement Time (h) | Photo-oxidative Stability Embrittlement Time (h) |
| --- | --- | --- |
| 0.3 | 580 | 1800 |
| 0.5 | 1100 | 2400 |

What is claimed is:

1. 4-spiro-oxirane derivatives of substituted piperidine having the formula:

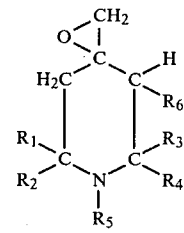

in which $R_1$, $R_2$, $R_3$, -- and $R_4$, either like or unlike one another, are each an alkyl radical containing 1 to 4 carbon atoms, or $R_1$ and $R_2$, and/or $R_3$ and $R_4$, together, form a cyclo-alkylene radical containing 3 to 12 carbon atoms;

$R_5$ is hydrogen, an alkyl, oxyalkyl or alkoxy radical containing 1 to 6 carbon atoms, an aryl or aryl-alkyl radical containing 6 to 18 carbon atoms; an alkenyl radical containing 2 to 6 carbon atoms or a $—(CH_2)_x-CO_2R_7$ radical, in which X is zero or an integer from 1 to 12 and $R_7$ is H, a metal selected from the alkaline metals, the alkaline-earth metals, and the transition metals, an alkyl, alkylene, alkenyl, alkenylene radical, each having 1 to 20 carbon atoms; and $R_6$ is hydrogen or an alkyl radical containing 1 to 4 carbon atoms.

2. 4-spiro-oxirane derivatives of substituted piperidine having formula (I) according to claim 1 and in which $R_5$ is a $—(CH_2)_x-CO_2R_7$ radical with $R_7$ being selected from the metals Ba, Ca, Na, K, Ni and Co.

3. 2,2,6,6-tetramethylpiperidine-4-spiro-oxirane having the formula:

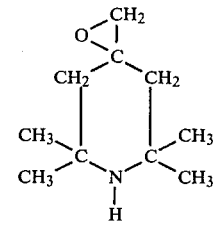

4. 1,2,2,6,6-pentamethylpiperidine-4-spiro-oxirane having the formula:

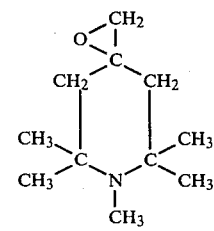

5. A process for preparing 4-spiro-oxirane derivatives of substituted piperidine according to claim 1, characterized in that it consists in reacting dimethylsulphonium methylide with the piperidone derivative, in the presence of an alkoxide or of a hydride of an alkaline metal.

6. The process of claim 5, in which dimethylsulphonium methylide is reacted with 2,2,6,6-tetramethylpiperidone.

7. The process of claim 5, in which the dimethylsulphonium methylide is reacted with 1,2,2,6,6-pentamethylpiperidone.

* * * * *